US009272027B1

(12) United States Patent
Lamkin et al.

(10) Patent No.: US 9,272,027 B1
(45) Date of Patent: Mar. 1, 2016

(54) FRANCISELLA TULARENSIS LIVE VACCINE STRAINS AND METHODS OF USE

(71) Applicant: The United States of America as Represented by the Secretary of the Air Force, Washington, DC (US)

(72) Inventors: Thomas J Lamkin, Fairfield, OH (US); Roland Saldanha, Dayton, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 14/480,071

(22) Filed: Sep. 8, 2014

(51) Int. Cl.
 *A61K 39/02* (2006.01)
 *A61K 49/00* (2006.01)
 *A61K 48/00* (2006.01)
 *C12N 15/74* (2006.01)
 *A61K 39/00* (2006.01)

(52) U.S. Cl.
 CPC ............ *A61K 39/0208* (2013.01); *C12N 15/74* (2013.01); *A61K 2039/522* (2013.01)

(58) Field of Classification Search
 CPC ............................... A61K 35/66; A61K 35/74
 USPC ........................ 424/9.1, 9.2, 93.2, 93.4, 234.1
 See application file for complete search history.

(56) References Cited

U.S. PATENT DOCUMENTS

| 5,698,421 | A | 12/1997 | Lambowitz et al. |
| 5,804,418 | A | 9/1998 | Lambowitz et al. |
| 6,001,608 | A | 12/1999 | Lambowitz et al. |
| 6,027,895 | A | 2/2000 | Lambowitz et al. |
| 8,323,664 | B2 | 12/2012 | Mitchell et al. |
| 2007/0264233 | A1 | 11/2007 | Michell et al. |
| 2010/0021501 | A1 | 1/2010 | Mitchell et al. |
| 2011/0020399 | A1 | 1/2011 | Santiago et al. |
| 2012/0082698 | A1 | 4/2012 | Conlan et al. |
| 2013/0122573 | A1 | 5/2013 | Mitchell et al. |

FOREIGN PATENT DOCUMENTS

| EP | 1610815 | 1/2006 |
| WO | 0129056 | 4/2001 |
| WO | 2004084935 | 10/2004 |
| WO | 2008012535 | 1/2008 |

OTHER PUBLICATIONS

Quarry, J.E., et al. Vaccine, vol. 25, No. 11, pp. 2011-2018, 2007.*
Bakshi et al., "Superoxide dismutase 8 gene (sodB)-deficient mutants of Francisella tularensis demonstrate hypersensitivity to oxidative stress and attenuated virulence," J Bacteriol., vol. 188 (2006) 6443-6448.
Buchan et al., "Identification of differentially regulated Francisella tularensis genes by use of a newly developed Tn5-based transposon delivery system," Appl. Environ Microbiol., vol. 74 (2008) 2637-2645.
Candales et al., "Database of bacterial group II introns," Nucleic Acids Research, vol. 40 (2012) D187-D190.
Conlan et al., "Vaccines against Francisella tularensis," Ann NY Acad. Sci., vol. 1105 (2007) 325-350.
Gallagher et al., "A comprehensive transposon mutant library of Francisella novidica, a bioweapon surrogate," PNAS, vol. 104 (Jan. 16, 2007) 1009-1014.
Kadzheav et al., "Identification of genes contributing to the virulence of Francisella tularensis SCHC S4 in a mouse intradermal infection model," PLoS One., vol. 4 (2009) 11 pages total.
Karberg et al., "Group II introns as controllable gene targeting vectors for genetic manipulation of bacteria" Nature Biotech., vol. 19 (2001) 1162-1167.
Kraemer et al., "Genome-wide screen in Francisella novicidia for genes required for pulmonary and systemic infection in mice," Infection and Immunity, vol. 77 (2009) 232-244.
Lambowitz et al., "Group II introns: mobile ribozymes that invade DNA," Cold Spring Harb Perspect Biol, vol. 3 (2011).
Lindemann et al., "Francisella tularensis Schu S4 O-antigen and capsule biosynthesis gene mutants induced early cell death in human macrophages," Infection and Immunity, vol. 79 (2011) 581-594.
Lovullo et al., "Single-copy chromosomal integration systems for Francisella tularensis," Microbiol., vol. 155 (2009) 1152-1163.
Maier et al., "Identification of Francisella tularensis Himar1-based transposon mutants defective for replication in macrophages," Infection and Immunity, vol. 75 (2007) 5376-5389.
Mann et al., "Rationally designed tularemia vaccines," Expert Rev Vaccines, vol. 8 (2009) 877-885.
Pechous et al., "Construction and Characterization of an Attenuated Purine Auxotroph in a Francisella tularensis live vaccine strain," Infection and Immunity, vol. 74 (2006)4452-4461.
Pechous et al., "Working toward the future: insitghts into Fracisella tularensis pathogenesis and vaccine development." Microbial Molec Bio Rev., vol. 73 (2009) 684-711.
Perutka et al., "Use of computer-designed group II introns to disrupt *Escherichia coli* DExH/D-box protein and DNA helicase genes," J Mol Biol., vol. 336 (2004) 421-439.
Raghunathan et al., "System approach to investigating host-pathogen interactions in infections with the biothreat agent Francisella. Contstraints-based model of Francisella tularensis," BMC Biotech., vol. 4 (2010) 19 pages total.

(Continued)

*Primary Examiner* — Rodney P Swartz
(74) *Attorney, Agent, or Firm* — AFMCLO/JAZ; Chastity Whitaker

(57) ABSTRACT

The present invention includes live strain of *Francisella tularensis* wherein a gene selected from the group consisting of priA and purA is inactivated. The present invention further includes a pharmaceutical composition comprising one or more live strains of *Francisella tularensis* according to the present invention and a pharmaceutically acceptable carrier. The present invention further includes a method of using one or more live strains of *Francisella tularensis* according to the present invention to confer immunity against a virulent strain of *Francisella tularensis*. The method comprises administering an effective amount of one or more live strains of *Francisella tularensis* according to the present invention or a pharmaceutical composition comprising one or more live *Francisella tularensis* strains to an animal such that an immune response is produced in the animal.

14 Claims, 7 Drawing Sheets

(56) References Cited

OTHER PUBLICATIONS

Rodriquez et al., "Targeted gene disruption in Francisella tularensis by group II introns,"Methods vol. 49 (2009) 270-274.

Rodriquez et al., "Targeted inactivation of Francisella tularensis genes by group II introns," Appl. Environ Microbiol., vol. 74 (2008) 2619-2626.

Saldanha et al., "Rapid targeted gene disruption in Bacillus anthracis," BMC Biotech., vol. 13 (2013).

Sigwart et al., "Effect of a purA mutation on efficacy of *Salmonella* live-vaccine vectors," Infect. Immun., vol. 57 (1989) 1858-1861.

Straskova et al., "Intracellular pathogenesis of Franscisella tularensis," Mil. Med. Sci. Lett., vol. 8 (2012) 27-39.

Tempel et al., "Attentuated Francisella novicida transposon mutants protect mice against wild-type challenges," Infect. Immun., vol. 74 (2006) 5095-5105.

Zhong et al., "Targeted and random bacterial gene disruption using a group II intron (targetron) vector containing a retrotransposition-activated selectable marker," Nucleic Acids Research, vol. 31 (2003) 1656-1664.

Zhuang et al, "Ecl5, a group IIB intron with high retrohoming frequency: DNA target site recongnition and use in gene targeting," RNA, vol. 15 (2009) 432-449.

Zimmerly et al., "Group II intron mobility occurs by target DNA-primed reverse transcription," Cell. vol. 82 (Aug. 25, 1995) 545-554.

\* cited by examiner

FIG. 5

SEQUENCE LISTING

<160> NUMBER OF SEQ ID NOS: 10

<210> SEQ ID NO 1
<211> LENGTH: 344
<212> TYPE: DNA
<213> ORGANISM: Artificial Sequence
<220> FEATURE:
<223> OTHER INFORMATION: T5 (priA) Intron Retargeting Sequence

<400> SEQUENCE: 1

```
ctcgagataa ttatccttaa ttagcagtca agtgcgccca gatagggtgt taagtcaagt      60
agtttaaggt actactctgt aagataacac agaaaacagc caacctaacc gaaaagcgaa     120
agctgatacg ggaacagagc acggttggaa agcgatgagt tacctaaaga caatcgggta     180
cgactgagtc gcaatgttaa tcagatataa ggtataagtt gtgtttactg aacgcaagtt     240
tctaatttcg gttctaatcc gatagaggaa agtgtctgaa acctctagta caaagaaagg     300
taagttaagt tgactgactt atctgttatc accacatttg taca                      344
```

<210> SEQ ID NO 2
<211> LENGTH: 344
<212> TYPE: DNA
<213> ORGANISM: Artificial Sequence
<220> FEATURE:
<223> OTHER INFORMATION: T116 (purA) Intron Retargeting Sequence

<400> SEQUENCE: 2

```
ctcgagataa ttatccttat tattcagatc agtgcgccca gatagggtgt taagtcaagt      60
agtttaaggt actactctgt aagataacac agaaaacagc caacctaacc gaaaagcgaa     120
agctgatacg ggaacagagc acggttggaa agcgatgagt tacctaaaga caatcgggta     180
cgactgagtc gcaatgttaa tcagatataa ggtataagtt gtgtttactg aacgcaagtt     240
tctaatttcg attaataatc gatagaggaa agtgtctgaa acctctagta caaagaaagg     300
taagttactt gatctgactt atctgttatc accacatttg taca                      344
```

<210> SEQ ID NO 3
<211> LENGTH: 26
<212> TYPE: DNA
<213> ORGANISM: Artificial Sequence
<220> FEATURE:
<223> OTHER INFORMATION: ISP-R (5' ISP)

<400> SEQUENCE: 3

```
actcagtcgt acccgattgt ctttag                                           26
```

<210> SEQ ID NO 4
<211> LENGTH: 23
<212> TYPE: DNA
<213> ORGANISM: Artificial Sequence
<220> FEATURE:
<223> OTHER INFORMATION: ISP-F (3' ISP)

<400> SEQUENCE: 4

```
cgttgggaaa tggcaatgat agc                                              23
```

<210> SEQ ID NO 5
<211> LENGTH: 26
<212> TYPE: DNA
<213> ORGANISM: Artificial Sequence
<220> FEATURE:
<223> OTHER INFORMATION: ISP*-R (5' ISP*)

<400> SEQUENCE: 5

```
aacagagcac ggttggaaag cgatga                                              26

<210> SEQ ID NO 6
<211> LENGTH: 26
<212> TYPE: DNA
<213> ORGANISM: Artificial Sequence
<220> FEATURE:
<223> OTHER INFORMATION: ISP*-F (3' ISP*)

<400> SEQUENCE: 6
agggtggtgc aaaccagtca cagtaa                                              26

<210> SEQ ID NO 7
<211> LENGTH: 20
<212> TYPE: DNA
<213> ORGANISM: Artificial Sequence
<220> FEATURE:
<223> OTHER INFORMATION: T5-F (priA GSP)

<400> SEQUENCE: 7
tattgggaag tgcaacacca                                                     20

<210> SEQ ID NO 8
<211> LENGTH: 21
<212> TYPE: DNA
<213> ORGANISM: Artificial Sequence
<220> FEATURE:
<223> OTHER INFORMATION: T5-R (priA GSP)

<400> SEQUENCE: 8
cactcaacaa cctcaccaca a                                                   21

<210> SEQ ID NO 9
<211> LENGTH: 26
<212> TYPE: DNA
<213> ORGANISM: Artificial Sequence
<220> FEATURE:
<223> OTHER INFORMATION: T116-F (purA GSP)

<400> SEQUENCE: 9
gagaaaatag gtacgactgg taaagg                                              26

<210> SEQ ID NO 10
<211> LENGTH: 19
<212> TYPE: DNA
<213> ORGANISM: Artificial Sequence
<220> FEATURE:
<223> OTHER INFORMATION: T116-R (purA GSP)

<400> SEQUENCE: 10
cgctgcaatt gcttgatct                                                      19
```

FRANCISELLA TULARENSIS LIVE VACCINE STRAINS AND METHODS OF USE

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

This invention relates generally to the field of vaccine strains. More particularly, it relates to attenuated strains of *Francisella tularensis* and methods of use thereof.

2. Description of the Related Art

*Francisella tularensis* (*F. tularensis*) is a Gram-negative coccobacillus with a natural reservoir that includes small mammals such as rabbits, hares, and rodents, as well as aquatic environments and soil. *F. tularensis* includes four subspecies—*tularensis* (type A), *holarctica* (type B), *novicida*, and *mediasiatica*—and the most virulent of these, *F. tularensis* subspecies *tularensis*, can cause infection with doses as low as 10 colony forming units (cfu). Transmission typically occurs via handling of infected animals and carcasses, consumption of contaminated food products, and occasionally through insect vectors. The strain and route of infection determines the progression of the disease, which generally involves spread to multiple organ systems and the lymphatic system. The U.S. Government currently classifies *F. tularensis* as a Tier 1 Select Agent, meaning that it has been determined to potentially pose a severe threat to human and animal health. Interest in the pathobiology of the bacterium has been rekindled with the recognition that *F. tularensis* may be deployed as a potent bioweapon due to its ease of dissemination via aerosolization and extremely low infective dose. Left untreated, *F. tularensis* has the potential to be lethal in 30-60% of infected individuals.

*F. tularensis* enters host macrophages and employs a variety of methods to evade host defense mechanisms throughout the infection cycle. The host immune system is evaded by a lipopolysaccharide (LPS) that interacts poorly with host pattern recognition receptors and does not induce inflammatory cytokines. In serum, *F. tularensis* binds Factor H to inactivate C3b by converting it to iC3b, which interferes with the formation of a membrane attack complex and opsonizes the bacterium to facilitate pathogen entry into the host by exploiting macrophages as a niche for replication. *F. tularensis*-containing phagosomes are arrested in the late endosomal stage and avoid fusion to lysosomes. The phagosome is transiently acidified leading to its disruption and escape of the bacteria into the cytosol. After replication in the cytoplasm, the bacteria induce autophagy and are released through apoptosis and pyroptosis.

Despite a generalized understanding of the *F. tularensis* infective cycle, more insight into the genes contributing to and controlling, for example, infection, intracellular survival, replication, pathogenicity, and effect on host immune response is needed for the development of effective vaccine and therapeutic countermeasures. An undefined vaccine strain of *F. tularensis* referred to as Live Vaccine Strain (LVS) was developed, which has demonstrated the ability confer at least partial immunity to challenges by *F. tularensis* subsp. *tularensis*. However, due to an incomplete understanding of the attenuation mechanism, presence of side effects, and other safety concerns, LVS has not been approved by the U.S. Food and Drug Administration for use as a vaccine.

In addition, a variety of methods such as random insertional mutagenesis using transposons, targeted gene replacement based on homologous recombination strategies, and targeted insertional inactivation using group II introns or targetrons have been used to mutagenize or disrupt *F. tularensis* genes and evaluate impact on intramacrophage survival and growth. Generation of transposon mutant libraries provide a high-throughput technique to screen for mutations that affect, for example, intramacrophage growth and virulence. However, the random nature of transposon insertions requires additional steps to ensure lack of hot spots and even distribution of insertions, as well as to determine the site of insertion and to demonstrate that a single insertion is responsible for the observed effects. Homologous recombination provides precise, targeted inactivation of genes but is difficult to adapt to high-throughput format. Use of targetrons combines the best aspects of transposon and homologous recombination techniques to provide a highly precise and easily adaptable method for disrupting and/or inactivating large numbers of genes throughout the genome.

SUMMARY OF THE INVENTION

The present invention includes a live strain of *Francisella tularensis* in which a gene selected from the group consisting of priA and purA is inactivated. In some embodiments, the gene is inactivated by an insertional mutation. In other embodiments, the gene is inactivated by deletion of at least a portion of the gene. In further embodiments, the live strain is selected from the group consisting of *Francisella tularensis* Schu4 and *Francisella tularensis* Live Vaccine Strain.

The present invention further includes a pharmaceutical composition comprising the live strain according to the present invention and a pharmaceutically acceptable carrier.

The present invention further includes a method of using a live strain of *Francisella tularensis* according to the present invention to confer immunity against a virulent strain of *Francisella tularensis* comprising administering a first effective amount of at least one of the live strains to an animal such that an immune response is produced in the animal. In some embodiments, the method further comprises administering a second effective amount of at least one of the live strains to an animal, in which the second effective amount is administered at a predetermined amount of time following administration of the first effective amount.

The present invention further includes a method of using a pharmaceutical composition according to the present invention to confer immunity against a virulent strain of *Francisella tularensis* comprising administering an effective amount of the pharmaceutical composition to an animal such that an immune response is produced in the animal.

BRIEF DESCRIPTION OF THE DRAWINGS

FIG. 5 is a graph demonstrating the results of an LDH assay of macrophages following infection by mutant T116 (SEQ ID NO. 2) of Schu4.

DETAILED DESCRIPTION OF THE INVENTION

Figure 1:
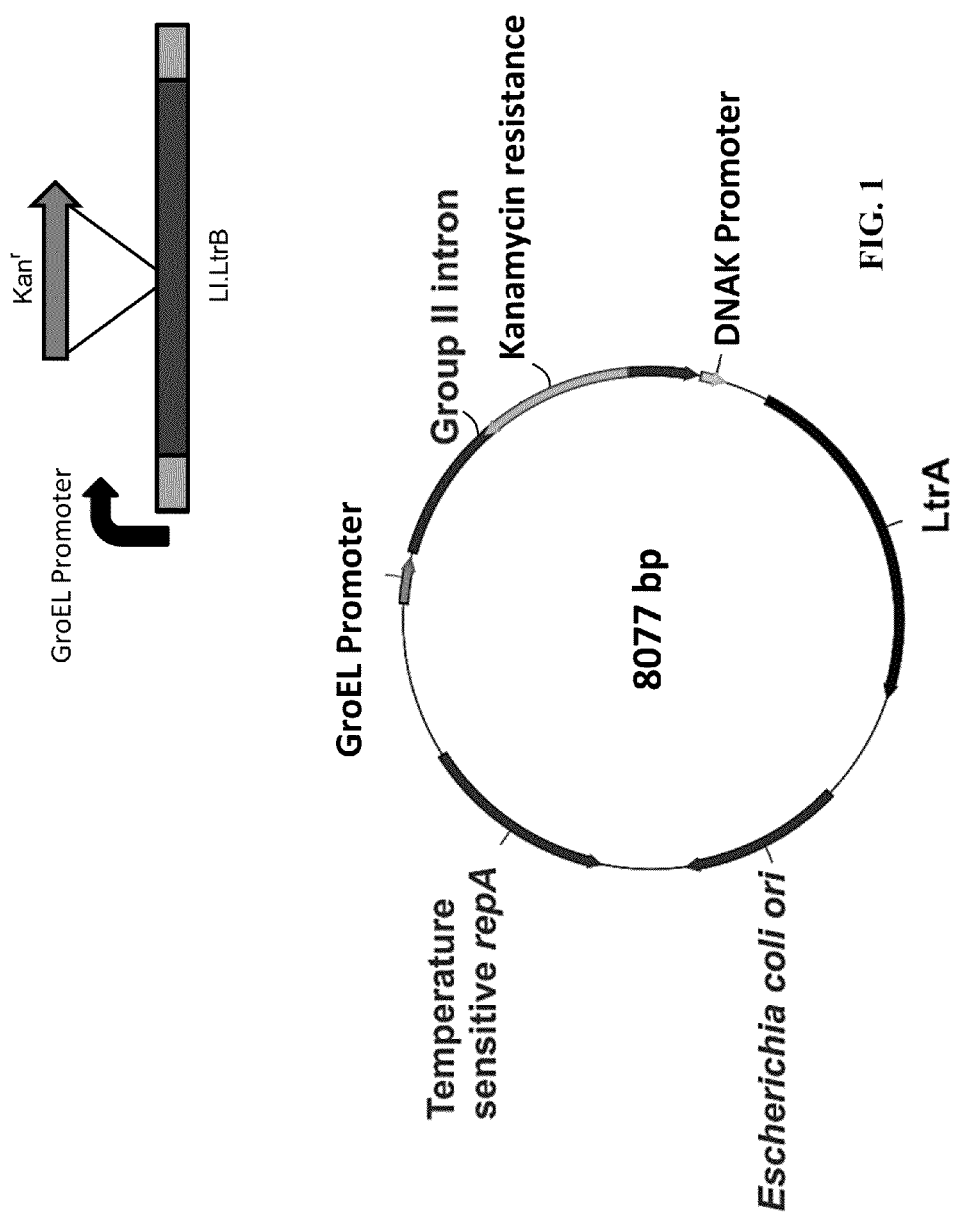
FIG. 1 is a representation of one embodiment of a plasmid vector for generating attenuated *F. tularensis* strains according to the present invention.

The present invention includes live, attenuated strains of *F. tularensis* and methods of using these strains alone or as part of a pharmaceutical composition to vaccinate a mammal against one or more virulent strains of *F. tularensis*. The presently disclosed vaccine candidate strains include attenuated mutant strains in which the priA or purA gene is disrupted. In some embodiments, the attenuated mutant may be derived from the highly virulent *F. tularensis* Schu4 strain. In other embodiments, the attenuated mutant may be derived from LVS or other suitable *F. tularensis* strain. Respiratory challenge with the attenuated mutants evoked a protective immune response that protected mice from subsequent challenge by wild type Schu4.

Vaccine strains according to the present invention may be used as medical vaccines, as well as research reagents. Live, attenuated vaccines are one of the best available proxies for a natural infection and thus elicit strong immune responses and often confer lifelong immunity quickly and with a small number of doses. In addition, the process of identifying vaccine strain candidates may help to identify new drug targets. For several *F. tularensis* genes, mutations could not be obtained, which suggests that these genes serve an essential function precluding their disruption or deletion. The utility of uncovering essential genes is that these genes may also provide unique antimicrobial targets, including identifying new targets for subunit vaccines. For example, one of the targets identified is the essential gene encoding gyrase, which is the target of the well-known fluoroquinone class of drugs. The elongation factor Tu is also essential and shares little homology with its eukaryotic counterpart, making it an attractive target for which four families of inhibitors exist and for which novel inhibitors are being uncovered. Other attractive targets include panC and the genes related to phosphoglucomutase, both of which appear to be essential in *F. tularensis* and non-essential in *Francisella novicida*. These inconsistencies serve to illustrate the value of using multiple approaches to query the functional importance of a gene.

For several other genes, no drug is available, but the experimentally demonstrated importance for bacterial survival suggests unique points of vulnerability that have been hitherto unexploited and may help to define novel paths to antimicrobial development. The network of protein-protein interactions deduced through bioinformatics tools can be matched against the network of essential genes to guide the potential prioritization of drug targets. The rapid generation of mutants also allows the evaluation of gene products in cell growth and survival. The present invention includes mutants that are severely attenuated yet still capable of inducing immunoprotection against pulmonary challenge with the wild type *F. tularensis* Schu4. The ability to rapidly and specifically disrupt genes by, for example, intron insertion in the select agent *F. tularensis* accelerates the pace of finding effective countermeasures, both drug and vaccine, to this potent pathogen. For example, large numbers of rationally designed attenuated variants can be tested for development of vaccines and then selected for dual knockout combinations to meet U.S. Food and Drug Administration requirements. The systematic interrogation of each gene's role in pathogenesis and intracellular replication accelerates the identification of core vulnerabilities in the pathogen that can be rationally targeted to develop effective novel therapeutics that cannot be easily subverted by engineered threats. This technology may accelerate countermeasure development as global communities continue to battle against the threat of bioweapons, drug resistance and emerging diseases.

Attenuated strains according to the present invention may be generated using one of several conventional methods, as well as novel methods disclosed here. In general, a vector targeted to a specific gene or area of the genome is introduced into the strain to generate a mutant by, for example, use of homologous recombination to delete all or part of the gene or introduce mutations that modify the function or expression of the gene. Those of ordinary skill in the art will appreciate that other suitable techniques may be employed to achieve deletion or interruption of one or more genes, such as the use of transposons and introns inactivate the gene via an insertional mutation.

In one embodiment, attenuated strains of *F. tularensis* according to the present invention may be generated using group II introns or targetrons. Normally found in organellar and bacterial genomes, group II introns belong to a class of autocatalytic ribonucleic acid (RNA) molecules that frequently encode proteins that facilitate the splicing and dispersal of the intron via retrotranspositon. These mobile introns have the ability to move to new genomic sites through a unique mobility mechanism, termed retrohoming. In the first step, the intron-encoded protein (IEP) uses a maturase activity to splice out the intron to which it remains associated, thus forming a ribonucleoprotein (RNP) complex comprising the intron and the IEP (also referred to as an intron integrase). This complex allows the intron to reverse splice into a deoxyribonucleic acid (DNA) target site.

Once the 3' end of the intron is covalently linked to the target DNA site, the IEP cleaves the antisense strand of the target DNA to generate a primer that is used to prime the copying of the intron via its own associated reverse transcriptase activity. The intron is then reverse transcribed, and insertion is completed by second strand synthesis and repair. Exon recognition of both DNA and RNA targets is guided by base pairing with exon binding sites (EBS) within the intron. Because of this guidance by EBS, it is easy to reprogram the intron insertion site simply by mutating the EBS. This technique affords the ability to systematically develop targeted genome-wide gene disruptions to elucidate the role of individual genes, particularly those of unknown function, and to provide targets for new therapeutic and vaccine candidates. To design the introns, each protein coding sequence of the entire bacterial genome is scanned for potential intron insertion sites using a computer algorithm derived from a learning set of successful intron integrations. The mutations necessary to retarget the intron to a desired site are either introduced through rounds of PCR mutagenesis or by total synthesis of the region to be exchanged.

The targetron is then introduced into an *F. tularensis* strain using, for example, an *E. coli* shuttle vector. In some embodiments, targetron-based methods of generating attenuated *F. tularensis* strains may include use of plasmids containing a temperature-sensitive origin and antibiotic resistance as described in more detail in Example 3. In other embodiments, the technique may include use of a retrotransposition activated marker as described in more detail in Example 4.

The deletion and/or disruption of one or more genes may be verified using a technique such as conventional PCR or real-time PCR (qPCR). Gene disruption/deletion has been verified using conventional PCR with primers flanking the site of insertion, followed by gel electrophoresis. This strategy is unattractive for work with select agents because it requires either preparation and aseptic removal of genomic DNA from a BSL3 facility or decontamination/disposal of large amounts of contaminated liquid waste from colony screening and conventional agarose gel-electrophoresis performed in the BSL3.

As an alternative, qPCR generates minimal waste and is compatible with a robotic workflow suitable for high-throughput verification of intron insertional mutations. Outward facing universal intron primers (ISP-R (SEQ ID NO. 3) and ISP-F (SEQ ID NO. 4)) are designed at the 5' and 3' flanks of the intron and paired with a 6-carboxyfluorescein (FAM)-labeled hydrolysis probe specific to either the 5' or 3' end of the intron. Appropriately designed gene-specific primers (GSP-F and GSP-R) flanking the intron insertion may be used to perform either conventional or real-time PCR with the universal intron-specific primers or the primer/hydrolysis probe set described herein. The qPCR assay allows multiplexing with the intron-specific probes and serves as a reference to distinguish failed PCR reactions from false negatives as well as a calibrant to guide scoring of true positives, all of which makes this approach readily applicable to screening bulk cultures with no further purification.

The present invention includes live, attenuated *F. tularensis* strains in which one or more of the genes involved with purine biosynthesis are inactivated. In some embodiments, the purA gene (for example, FTT0204 in *F. tularensis* subsp. *tularensis* Schu4), which encodes adenylosuccinate synthetase, is inactivated. The present invention further includes live, attenuated *F. tularensis* strains in which one or more of the genes involved with DNA replication. In some embodiments, the priA gene (for example, FTT0215 in *F. tularensis* Schu4 and FTL1943 in LVS), which encodes primosomal protein N', is inactivated. In some embodiments, the inactivation of the gene is obtained by an insertional mutation, and in other embodiments, inactivation is obtained by deletion of the entire gene or a portion thereof. As illustrated herein, strains of *F. tularensis* in which the purA or priA gene are inactivated may protect against aerosol challenge from the virulent *F. tularensis* Schu4 strain.

The present invention further includes methods of using live, attenuated strains according to the present invention to vaccinate an animal, including a human being, against infection by *F. tularensis* and to treat an infection by *F. tularensis*. The method comprises administering an effective amount of one or more live, attenuated *F. tularensis* strains to the animal such that an immune response is produced in the animal. In some embodiments, the priA gene of the attenuated *F. tularensis* strain is inactivated. In other embodiments, the purA gene of the attenuated *F. tularensis* strain is inactivated. In further embodiments, the priA or purA gene are inactivated by an insertional mutation or deletion of all or part of the gene.

The present invention further includes methods of vaccinating an animal against infection by *F. tularensis* or treating an infection caused by *F. tularensis* by administering an effective amount of a pharmaceutical composition comprising one or more live, attenuated strains of *F. tularensis* according to the present invention and a pharmaceutically acceptable carrier. The pharmaceutically acceptable carrier will vary based on the desired method or route of administration and may comprise any suitable liquid, semisolid, or solid known in the art. For example, the carrier may comprise sterile water or saline. The carrier may further comprise, for example, a diluent or other additive necessary to ensure stability of the composition and/or facilitate administration of the composition. Those of ordinary skill in the art will appreciate that there are many additional suitable carriers and compositions that may be used.

The live, attenuated *F. tularensis* strain(s) with or without a carrier may be administered using any suitable method, including, but not limited to, intradermal, intramuscular, intravenous, oral, or intranasal administration, as well as by scarification. In some embodiments, the method may further comprise administering a second dose of the live, attenuated *F. tularensis* strain(s) with or without a carrier at a predetermined time following the initial administration. This booster dose may help to increase the immune response of the animal and provide further protection against or treatment of *F. tularensis* infection.

The following examples and methods are presented as illustrative of the present invention or methods of carrying out the invention, and are not restrictive or limiting of the scope of the invention in any manner.

Example 1

Plasmid Construction

Previous targetron-based systems had no means to select for intron insertion and required laborious screening to find gene disruptions. To enhance the efficiency of screening, a construct with a kanamycin resistance cassette on a ts replicon was developed to deliver a group II intron targeted to a desired gene. In the first step, PCR was used to amplify a kanamycin resistance marker driven by FTN1451 from plasmid pKEK1140 and cloned into the neutral MluI site of a derivative of pKEK1140, resulting in a plasmid with two copies of kanamycin resistance (one within the intron). In a second step the duplicated kanamycin resistance marker residing outside of the intron was deleted by cleaving the plasmid with NgoMIV and NotI to release the marker. The resulting overhangs were filled in to create blunt ends, and the linearized vector was recircularized by ligation to create the exemplary ts targetron shown in FIG. 1. The *Lactococcus lactis* group II intron and L1.LtrB intron encoded protein are expressed from a GroEL promoter. The inset shows the area of the intron and kanamycin resistance cassette in more detail. The kanamycin resistance marker was introduced into the neutral MluI site within the L1.LtrB group II intron, while simultaneously deleting all plasmid borne selection markers.

A retrotransposition activated kanamycin marker was commercially synthesized (GenScript). The design features include a select agent-compliant, CDC-approved kanamycin resistance marker with codons optimized for expression in organisms with a low GC content. The expression of the kanamycin resistance gene was initially driven by an endogenous kanamycin resistance promoter and a group I intron from td, which is inserted between codons 15 and 16. In subsequent embodiments, an *F. tularensis* sodB promoter, a highly expressed gene that is known to be essential to the full virulence of *F. tularensis*, was cloned into the MluI site of cloning vector pKEK1140, which replaced the endogenous promoter driving the kanamycin resistance marker. Base pairing of the internal guide sequence of the td intron was optimized through a round of site-directed mutagenesis to yield pRSFT1 (shown in FIG. 2). The inset shows the area of the td intron and kanamycin resistance marker in more detail.

Figure 2:
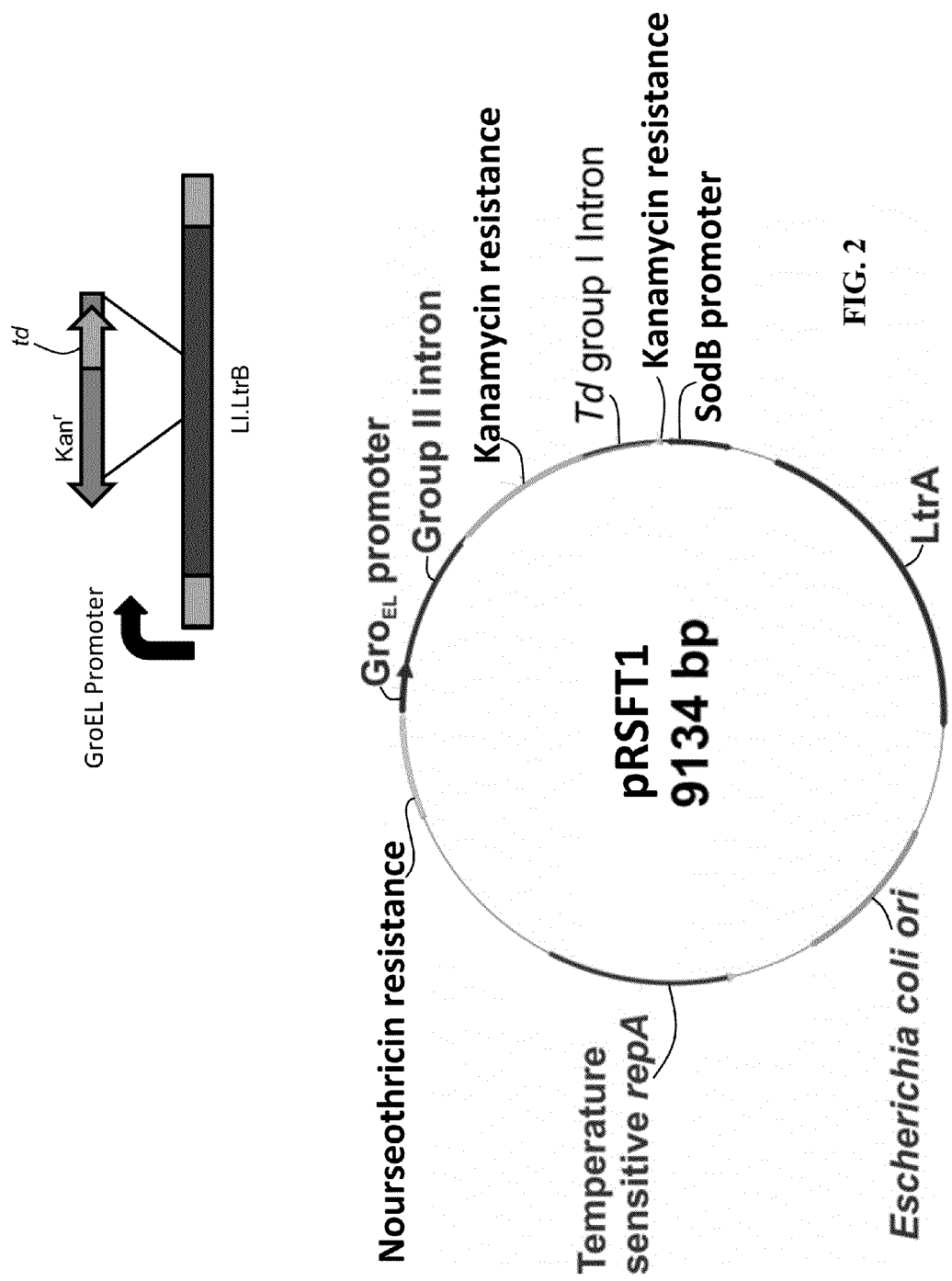
FIG. 2 is a representation of another embodiment of a plasmid vector for generating attenuated *F. tularensis* strains according to the present invention.

For plasmids utilized in the retrotransposition activated kanamycin marker method, the kanamycin resistance marker is cloned in an antisense direction to the group II "targeting" intron transcribed from the *F. tularensis* sodB promoter as shown in FIG. 2. The coding sequence of the kanamycin drug resistance marker is interrupted by a self-splicing td group I intron. The *Lactococcus lactis* group II intron and Ll.LtrB intron encoded protein are expressed from a GroEL promoter. A nourseothricin resistance marker was amplified using polymerase chain reaction (PCR) primers that added NdeI and NotI restriction sites to the 5' and 3' ends of the resistance cassette. The amplified nourseothricin cassette was cleaved with NdeI and NotI and cloned into pRSFT1, which had been cleaved with the same enzymes. Plasmid variants with the +1 position of the intron changed to either G, A, T, or C were generated through site-specific mutagenesis. The area of the intron controlling the IBS/EBS interaction site was designed to be exchanged as XhoI-BsrGI sites. To accommodate this modification, an interfering BsrGI site was eliminated either through site-directed mutagenesis (GenScript) or via partial digestion with BsrGI, thereby filling in the resulting overhang. Elimination of the intended BsrGI site was confirmed by DNA sequencing.

Example 2

Creation of Mutant Strains

*F. tularensis* LVS::superfolder or *F. tularensis* Schu4::superfolder was inoculated onto chocolate agar. A single colony was used to inoculate 2 ml of TSB+0.1% cysteine and grown at 37° C. overnight. The overnight culture was diluted into 50 ml of TSB+0.1% cysteine and grown to exponential phase (optical density of 0.3-0.6 at $OD_{550}$ nm), washed twice with 0.5 M sucrose (Boehringer Mannheim Biochemicals), and suspended in 1 ml of 0.5 M sucrose to obtain a concentration of $1 \times 10^{10}$ cells $ml^{-1}$.

Genes may be selected for inactivation by retargeting the intron and designing suitable intron sequences using a targeting algorithm described in Perutka, Jiri, et al., "Use of Computer-Designed Group II Introns to Disrupt *Escherichia coli* DExH/D-box Protein and DNA Helicase Genes," J Mol Biol, 336:421-439, 13 Feb. 2004. Following design of the desired plasmid, the plasmid is introduced into the *F. tularensis* strain. For electroporation, 1 µl of plasmid DNA (100 µg/ml) was mixed with a 200 µl suspension of electrocompetent cells, incubated at room temperature for 10 min, and electroporated in a 0.2-cm cuvette by using the following gene pulser settings: 2.5 kV, 25 µF, and 600Ω. Immediately after electroporation, cells were suspended in 1 ml of MH or TSB+0.1% cysteine broth and incubated at the appropriate temperature (30° C. or 37° C.) for 4 hours (*F. tularensis* LVS) or overnight at 30° C. to allow for targeted intron integration to occur.

Example 3

Temperature-Sensitive (ts) Replicon-Based Screening

Following introduction of the plasmid via electroporation and growth at a permissive temperature, the cells were then serially passaged at the restrictive temperature of 37° C. and then plated at 37° C. on Cysteine Heart Agar+Blood (CHAB) containing kanamycin. Kanamycin-resistant colonies are presumptive integrants because the ts plasmid is anticipated to be cured during culture at the restrictive temperature. Only cells with the intron expressing the kanamycin resistance gene stably integrated through intron insertion at its chromosomal target are expected to remain kanamycin-resistant. The intron-based kanamycin marker and ts origin enriches for insertion events, making the subsequent PCR-based validation more efficient.

Approximately 25% (4/16) of the kanamycin-resistant colonies possessed insertions at the correct genomic target site as confirmed by DNA sequencing of the PCR products (not shown). Of the 29 mutants attempted using this strategy, 12 were obtained (not shown). For the positive insertions obtained, the frequency of intron insertion ranged from as high as 100% positive to as low as 0.5%. For the majority of insertions (8 of 12), less than 10 colonies were screened to obtain the desired gene inactivation via intron insertion. For the remaining genes of interest, it became apparent that curing of the ts plasmid was likely not reliable. Despite multiple rounds of growth at the restrictive temperature, all kanamycin-resistant colonies proved to have retained the plasmid, making this approach less reliable and potentially limited in its utility for high-throughput intron-directed gene disruption.

Example 4

Screening Using the Retrotransposition Activated Selectable Marker Method

To address the potential limitations of is plasmid curing described in Example 3, a "RAM" (retrotransposition activated marker) kanamycin marker is used to enable direct selection of disruptants in *F. tularensis* species. The plasmid donor DNA copy is functionally kanamycin-sensitive because it is interrupted by the group I intron. When transcribed, the td intron interrupting the kanamycin cassette is spliced out, and the resulting RNA can be used as a substrate for retrotransposition. The RAM method ensures that an uninterrupted copy of the kanamycin cassette integrates into the chromosome upon intron insertion via retrotransposition. Thus, successful targetron insertions are easily and reliably selected through acquisition of resistance to kanamycin.

As a proof of principle, 96 genes were selected for inactivation by retargeting the intron using the previously described targeting algorithm. The range of genes targeted for inactivation is broad and includes genes involved in RNA and DNA metabolism, intermediary metabolism, stress proteins, transcriptional regulators, and conserved hypothetical proteins. Following electroporation, nourseothricin-resistant colonies were propagated on chocolate agar+nourseothricin 50 µg/ml at 30° C. to allow time for the targetron to express and perform the integration reaction. A pool of each culture was then plated on CHAB+kanamycin plates to directly select for integration events. Putative candidates with gene disruptions resulting from intron insertion were recovered on kanamycin plates due to activation of the kanamycin reporter by retrotransposition. The frequency of kanamycin resistant colonies ranged from a near lawn to rare isolated colonies, reflecting the efficiency with which the site-specific intron integration occurs.

To estimate the frequency of intron insertion, 10 representative transformants from the collection of 96 original constructs were grown to near confluency at 30° C. (the permissive temperature for plasmid replication) on chocolate agar plates containing nourseothricin. After approximately 48 hours of growth, the colonies were resuspended, and an estimate of cell counts was made via measurement of the $OD_{600}$. Suitable dilutions of the cultures were plated on CHAB containing either nourseothricin or kanamycin. The frequency of intron insertion can be estimated from the frequency of kanamycin-resistant colonies relative to the total number of nourseothricin-resistant colonies. Table 1 shows that the frequency of insertion ranges from $10^{-5}$ to $10^{-9}$. Even in cases of low frequency, the strong selection allows plating of a large number of bacteria and isolation of relatively rare integration events. The ability to select for integration events is an important tool that may allow targeted genome-wide disruptions in *F. tularensis* and subsequent creation of ordered disruptant libraries, thereby enabling investigation of individual genes and their role in pathogenesis.

TABLE 1

Group II Insertion Frequency of Select Mutants[a]

| Ft LVS Mutant | Experiment 1 | Experiment 2 | Experiment 3 |
|---|---|---|---|
| T3  | 1.0E−06 | 2.0E−06 | 4.0E−06 |
| T22 | 6.6E−05 | 5.0E−05 | 5.0E−05 |
| T29 | 1.5E−08 | 3.2E−08 | 5.7E−08 |
| T34 | 4.4E−08 | N/A[b]  | N/A     |
| T59 | 4.2E−09 | 9.0E−09 | 2.2E−08 |
| T64 | 3.3E−09 | N/A     | N/A     |
| T76 | 6.4E−08 | N/A     | N/A     |
| T81 | 1.4E−04 | 7.0E−06 | 2.0E−06 |
| T77 | 2.0E−08 | N/A     | N/A     |
| T96 | N/A     | 2.5E−06 | 7.7E−07 |

[a]Calculated by dividing the frequency of intron insertion events by total colonies counted.
[b]N/A, mutant not tested in this experiment.

Example 5

Confirmation of Intron Insertion by PCR

Kanamycin-resistant candidates were assessed by conventional and/or qPCR using primers flanking the site of chromosomal insertion. In some cases, cells were picked from colonies using sterile pipet tips and used directly in reaction mixtures for conventional and qPCR. In other cases, cells from kanamycin-resistant colonies were inoculated into TSB+0.1% cysteine broth and incubated overnight. 1 µl of broth culture was then used directly in the PCR assays. Specific primers flanking the site of chromosomal insertion were designed using BatchPrimer3 and synthesized by Integrated DNA Technologies®. Primers flanking the site of chromosomal insertion were matched with universal primers within the intron to amplify the junction of the 5' and 3' intron and the genome. For qPCR, successful amplification was followed by two ZEN™ double-quenched probes designed to hybridize with the 5' and 3' ends of the targetron.

For conventional PCR, DNA was amplified using 1 µl of LongAmp® Taq DNA Polymerase (New England Biolabs®), 2.5 µl of 5× LongAmp® Taq Reaction Buffer, 0.4 µl of 10 mM dNTP Mix (New England Bioloabs®), nuclease-free water (Ambion®), 200 nM of each primer, and whole cell template in a final volume of 12.5 µl per reaction. The following cycling conditions were used: initial denaturation at 94° C. for 30 sec; followed by 30 cycles of denaturation at 94° C. for 30 sec, annealing at 60° C. for 45 sec and extension at 65° C. for 3 min; and a final extension at 65° C. for 10 min. Products were visualized using 1% ethidium bromide (Fisher Bioreagents®) on a 1% agarose gel.

qPCR was performed using 10 µl of 2× Probes Master reagent (Roche®), 50 nM ROX™ Passive Reference Dye (Affymetrix®), nuclease-free water (Ambion®), 200 nM of each primer, and 50 nM of probe in a final volume of 20 µl. Whole cell template was added to each reaction, and cycling was performed using an ABI Fast Real-Time 7500 (Applied Biosystems®) platform as follows: polymerase activation at 95° C. for 10 min, followed by 40 cycles of denaturation at 95° C. for 3 sec and annealing/extension at 60° C. for 2 min 30 sec. Results were analyzed using ABI 7500 Fast System SDS software (Applied Biosystems®).

The 96 genes selected in Example 4 were screened using one or both PCR assays to search for gene-specific intron insertion. In the LVS strain, 62 of the 96 total targeted sites have been disrupted; 20 of these sites appear very inefficient for disruption and 12 introns presumably. For the same set of intron donors in Schu4, 60 insertions were obtained; the same 12 introns mistargeted and another set of 12 appear to be inefficient (data not shown). To determine whether each intron is inserted at a unique site in the *F. tularensis* genome, genomic DNA from the wild type strain and 15 independent insertion events was isolated. The isolated DNA was then digested with HindIII (an enzyme that does not cut within the intron) and subjected to Southern blot analysis using a chemiluminescent intron probe. A unique HindIII genomic fragment was detected for each intron insertion (not shown), which indicates that the designed introns integrate specifically and uniquely at a specific locus.

Example 6

Design, Creation, and Verification of purA and priA Mutants

*F. tularensis* strains with insertional mutations in the priA and purA genes were generated according to the present invention. Table 2 lists the sequences used to retarget the intron to the intended insertion site and the PCR primer sequences used to verify intron insertion. In the intron retargeting sequences, the underlined sites are the restriction sites for XhoI and BsrGI, and the portions in bold are the sequences that were altered to retarget the intron to the intended insertion site.

The targeting and design algorithm as described herein was used to generate the intron insertion sequences designed to create insertional mutants in either the priA or purA gene. The insertions for both mutations were then verified using PCR primers flanking the site of intron insertion and conventional PCR (data not shown). As described herein, universal intron specific primers (ISP-R (SEQ ID NO. 3) and ISP-F (SEQ ID NO. 4)) are used in conjunction with gene-specific primers flanking the intron insertion. Verification performed with qPCR may utilize the ZEN™ double-quenched intron specific probes (ISP*-R (SEQ ID NO. 5) and ISP*-F (SEQ ID NO. 6)) specific to either the 5' or 3' end of the intron.

TABLE 2

Sequences Used to Create and Verify priA and purA Mutants

| Seq Name & Type | SEQ ID NO | Sequence |
|---|---|---|
| T5 (priA) Intron Retargeting Sequence (SEQ ID NO. 1) | 1 | <u>CTCGAG</u>ATAATTATCCTTAATTAGCAGTCAAGTGCGCCCAGATAGGGTGTTAAGTCAAGTAGTTTAAGGTACTACTCTGTAAGATAACACAGAAAACAGCCAACCTAACCGAAAAGCGAAAGCTGATACGGGAACAGAGCACGGTTGGAAAGCGATGAGTTACCTAAAGACAATCGGGTACGACTGAGTCGCAATGTTAATCAGATATAAGGTATAAGTTGTGTTTACTGAACGCAAGTTTCTAATTTCGGTTCTAATCCGATAGAGGAAAGTGTCTGAAACCTCTAGTACAAAGAAAGGTAAGTTAAGTTGACTGACTTATCTGTTATCACCACATT<u>TGTACA</u> |

TABLE 2-continued

| Sequences Used to Create and Verify priA and purA Mutants | | |
|---|---|---|
| Seq Name & Type | SEQ ID NO | Sequence |
| T116 (purA) Intron Retargeting Sequence (SEQ ID NO. 2) | 2 | CTCGAGATAATTATCCTTATTATTCAGATCAGTGCGCCCAGATAGGGTGTTAAGTCAAGTAGTTTAAGGTACTACTCTGTAAGATAACACAGAAAACAGCCAACCTAACCGAAAAGCGAAAGCTGATACGGGAACAGAGCACGGTTGGAAAGCGATGAGTTACCTAAAGACAATCGGGTACGACTGAGTCGCAATGTTAATCAGATATAAGGTATAAGTTGTGTTTACTGAACGCAAGTTTCTAATTTCGATTAATAATCGATAGAGGAAAGTGTCTGAAACCTCTAGTACAAAGAAAGGTAAGTTACTTGATCTGACTTATCTGTTATCACCACATTTGTACA |
| ISP-R (5' ISP) (SEQ ID NO. 3) | 3 | ACTCAGTCGTACCCGATTGTCTTTAG |
| ISP-F (3' ISP) (SEQ ID NO. 4) | 4 | CGTTGGGAAATGGCAATGATAGC |
| ISP*-R (5' ISP*) (SEQ ID NO. 5) | 5 | 6-FAM - AACAGAGCA - ZEN - CGGTTGGAAAGCGATGA - IABkFQ |
| ISP*-F (3' ISP*) (SEQ ID NO. 6) | 6 | 6-FAM - AGGGTGGTG - ZEN - CAAACCAGTCACAGTAA - IABkFQ |
| T5-F (priA GSP) (SEQ ID NO. 7) | 7 | TATTGGGAAGTGCAACACCA |
| T5-R (priA GSP) (SEQ ID NO. 8) | 8 | CACTCAACAACCTCACCACAA |
| T116-F (purA GSP) (SEQ ID NO. 9) | 9 | GAGAAAATAGGTACGACTGGTAAAGG |
| T116-R (purA GSP) (SEQ ID NO. 10) | 10 | CGCTGCAATTGCTTGATCT |

Example 7

Growth Rates of Selected Mutants

Growth rate measurements were obtained as an initial assessment of the effect of gene disruption in multiple mutant strains. The mutant strains were grown on CHAB, resuspended in PBS, and the culture density measured by $OD_{600}$. Inoculations were performed in TSB supplemented with 0.1% cysteine, and the $OD_{600}$ was adjusted to 0.1. Quadruplicate samples of a superfolder GFP-tagged wild type strain (Applied Microbiology and Biotechnology® PMID: 23852642) or the mutant derivative were inoculated into 96 well plates and placed in a BioTek® Synergy™ 2 instrument maintained at 37° C. with shaking $OD_{600}$ measurements were obtained at 20-minute intervals over a 24-hour growth period.

The mutants differ in both their lag and exponential phase growth rate, and in final OD at saturation (data not shown). Table 3 summarizes some of the data from the growth studies. The doubling time in TSB-C for the wild type superfolder was approximately 8.84 hours, while the mutant doubling times ranged from 5.13 to 19.79 hours.

TABLE 3

| Average Growth Rate and Doubling Time of Selected Mutants | | |
|---|---|---|

Figure 3:
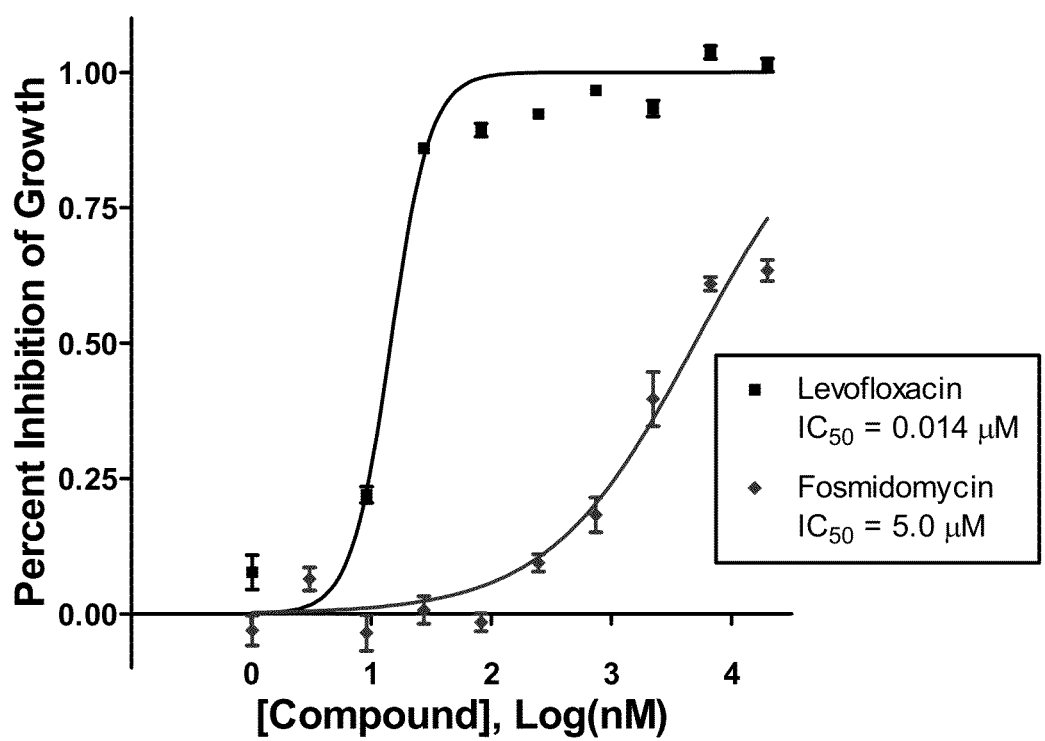
FIG. 3 is plot showing growth inhibition of *F. tularensis* by fosmidomycin and levofloxacin.

| Mutant | Average Growth Rate ($h^{-1}$) | Average Doubling Time (h) |
| T0113 | 0.14 | 5.13 |
| T0893 | 0.13 | 5.16 |
| T584 | 0.13 | 5.18 |
| T61 | 0.13 | 5.30 |
| T78 | 0.13 | 5.37 |
| T0291 | 0.13 | 5.51 |
| T1181 | 0.12 | 5.88 |
| T19 | 0.11 | 6.27 |
| T5 | 0.09 | 7.37 |
| T68 | 0.09 | 7.60 |
| T22 | 0.09 | 7.63 |
| FTL 1018 | 0.09 | 7.81 |
| FTL 0690 | 0.09 | 7.94 |
| FTT 1105 | 0.09 | 8.20 |
| T74 | 0.08 | 8.75 |
| LVS SF | 0.09 | 8.84 |
| T76 | 0.08 | 8.85 |
| T27 | 0.08 | 9.20 |
| T73 | 0.07 | 9.75 |
| T75 | 0.07 | 9.77 |
| T71 | 0.07 | 9.81 |
| FTT 0113 | 0.07 | 9.85 |
| T86 | 0.07 | 10.00 |
| T77 | 0.07 | 10.14 |
| T1 | 0.07 | 10.34 |
| T85 | 0.06 | 10.74 |
| T20 | 0.08 | 10.92 |
| T7 | 0.07 | 11.04 |
| T28 | 0.06 | 11.19 |
| T83 | 0.06 | 11.22 |
| T9 | 0.08 | 11.33 |
| T81 | 0.06 | 11.74 |
| T95 | 0.06 | 11.87 |
| T43 | 0.09 | 11.93 |
| T70 | 0.06 | 12.13 |
| T84 | 0.06 | 12.24 |
| T0989 | 0.06 | 12.52 |
| T2 | 0.06 | 12.55 |
| T82 | 0.06 | 12.56 |
| T13 | 0.05 | 12.65 |
| T3 | 0.06 | 13.78 |
| FTL 0217 | 0.05 | 14.04 |
| FTL 0092 | 0.05 | 14.58 |
| T10 | 0.05 | 14.73 |
| T18 | 0.04 | 15.96 |
| T30 | 0.04 | 16.38 |
| T16 | 0.04 | 16.86 |
| T49 | 0.04 | 18.65 |
| T12 | 0.04 | 18.67 |
| T23 | 0.04 | 19.06 |
| T15 | 0.04 | 19.18 |
| FTL 0714 | 0.04 | 19.34 |
| T69 | 0.04 | 19.79 |

Example 8

Identifying New Antimicrobial Targets

For several genes, it proved impossible to generate a targetron insertion, which could either be because the gene is essential and therefore does not yield viable cells if disrupted or the designed targetron functioned poorly. For many of these genes, the assumption that the gene is essential agrees with data from *F. novicida* transposon insertions (data not shown). In other cases, the gene was dispensable in *F. novicida*, but evidence in other bacterial pathogens suggests the gene is essential. Therefore, this approach may be useful to identify new therapeutic targets or reposition known drugs.

For example, the RAM method identified IspG is an essential gene in *F. tularensis* Schu4. IspG is known to be involved in isoprenoid biosynthesis using the non-mevalonate pathway that is a unique bacterial biosynthetic pathway. IspG is thus emerging as the target for several novel antimicrobials that also may find utility in combating several drug resistant pathogens. A known isoprenoid pathway inhibitor, fosmidomycin, was tested for its effect on growth of *F. tularensis* Schu4. Serial dilutions of fosmidomycin and levofloxacin in DMSO were prepared in 384-well clear bottom microplates. The compounds were diluted in Mueller-Hinton broth supplemented with 2% IsoVitalex® to give a final compound concentration of 0.001-20 μM and an overall DMSO concentration of 0.1%. The wells were inoculated with 10 μL of a *F. tularensis* Schu4 GFP suspension (1.25×108 CFU/mL in PBS), and the plates were incubated in a 37° C. shaking incubator. After a 44 hour incubation period, the $OD_{600}$ was measured for all wells. The percent inhibition of *F. tularensis* growth was calculated relative to the DMSO-treated control wells. FIG. 3 shows that *F. tularensis* Schu4 growth is inhibited with an $IC_{50}$ of 5 μM of fosmidomycin, which correlates with the identification of IspG as an essential gene. The rapid ability to identify essential genes in this pathogen allows for experimental validation of the value of potential drug targets as described herein.

Example 9

Evaluation of Attenuated Mutants as Vaccine Candidates Using an MDM Infection Model An ex vivo assessment of the impact of specific targetron mutations in a monocyte-derived macrophage (MDM) infection model was performed. For this, human MDM (hMDM) were infected with the wild type or a targetron mutant at an MOI of 50 for 90 minutes. The cells were washed to remove extracellular bacteria and incubated at 37° C. for 30 hours to allow the intracellular life cycle to progress. After incubation, the cells were then stained with Hoechst 33342 nuclear stain and LIVE/DEAD® Fixable Far Red Dead Cell stain (Molecular Probes® Inc.) prior to fixation for analysis. The fixed cells were visualized using an ImageXpress® Ultra High Content Imaging microscope (Molecular Devices®).

Figure 4:
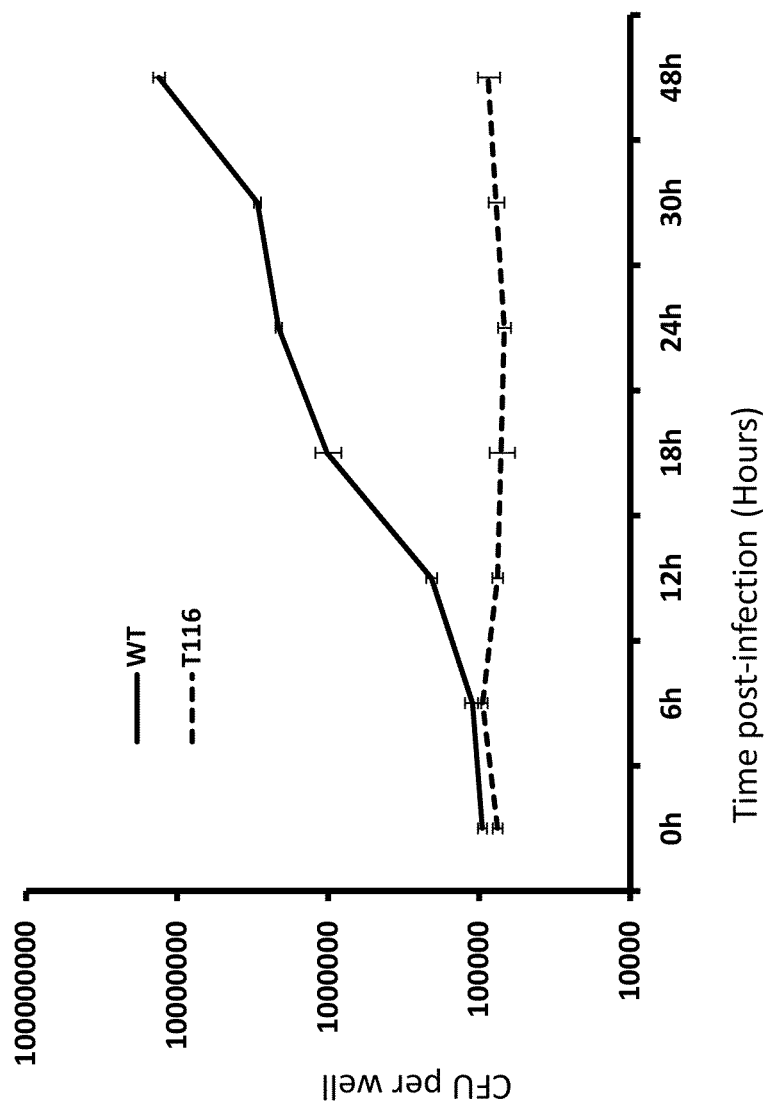
FIG. 4 is a graph demonstrating a time course of infection of lysed macrophages following infection by mutant T116 (SEQ ID NO. 2) of Sch4 (disruption of purA gene).
Figure 5:
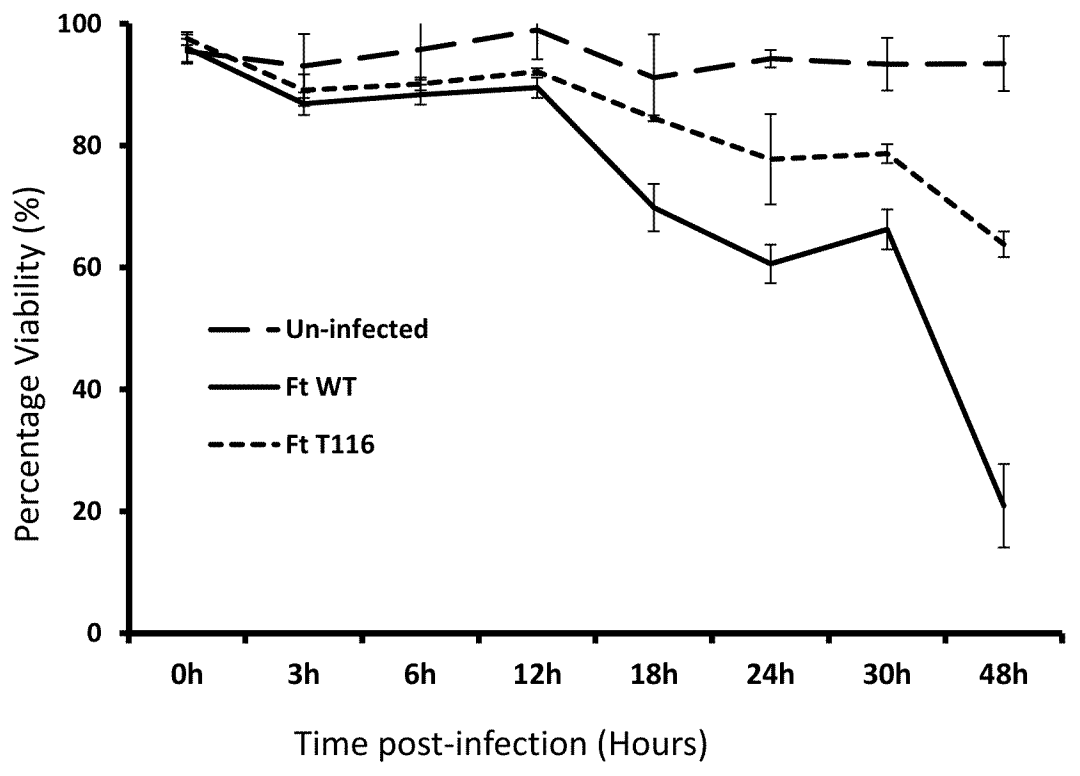

Using this assay, mutants defective for intracellular replication were identified. To characterize these mutants further, MDMs were infected with the wild type or a mutant at an MOI of 50. Uninfected cells were washed away and at several points post-infection, the wells were (1) lysed with 0.1% SDS and plated on CHAB to determine bacterial cell counts; (2) assayed for lactate dehydrogenase (LDH) as a measure of viability; or fixed and stained. FIG. 4 shows an assay for mutant T116 of Schu4 (disruption of purA gene) (SEQ ID NO. 2) demonstrating a time course of infection of lysed macrophages, and FIG. 5 shows the results of an LDH assay with the same mutant at several time points post-macrophage infection. In FIGS. 4 and 5, it can be seen that mutant T116 (SEQ ID NO. 2) does not undergo the same replicative burst that the wild type did and was slow to kill macrophages. An additional mutant, mutant T5 in LVS (disruption of priA) (SEQ ID NO. 1), was also shown to be similarly replicatively impaired (data not shown).

Example 10

Evaluation of Attenuated Mutants as Vaccine Candidates Using a Mouse Infection Model Assays were conducted to evaluate the virulence of the *F. tularensis* LVS mutant T5 (priA) (SEQ ID NO. 1) and the *F. tularensis* Schu4 mutant T116 (purA) (SEQ ID NO. 2) in comparison to that of wild type *F. tularensis* Schu4 using a mouse infection model. Each strain (either mutant or wild type) being tested was administered to the murine respiratory system using an inhalation gasp reflex protocol. Lethal infectious doses used in this protocol, were determined to be an $LD_{100}$ of ~5,000 cfu for wild type LVS and an $LD_{100}$<10 cfu for Schu4.

Figure 6:
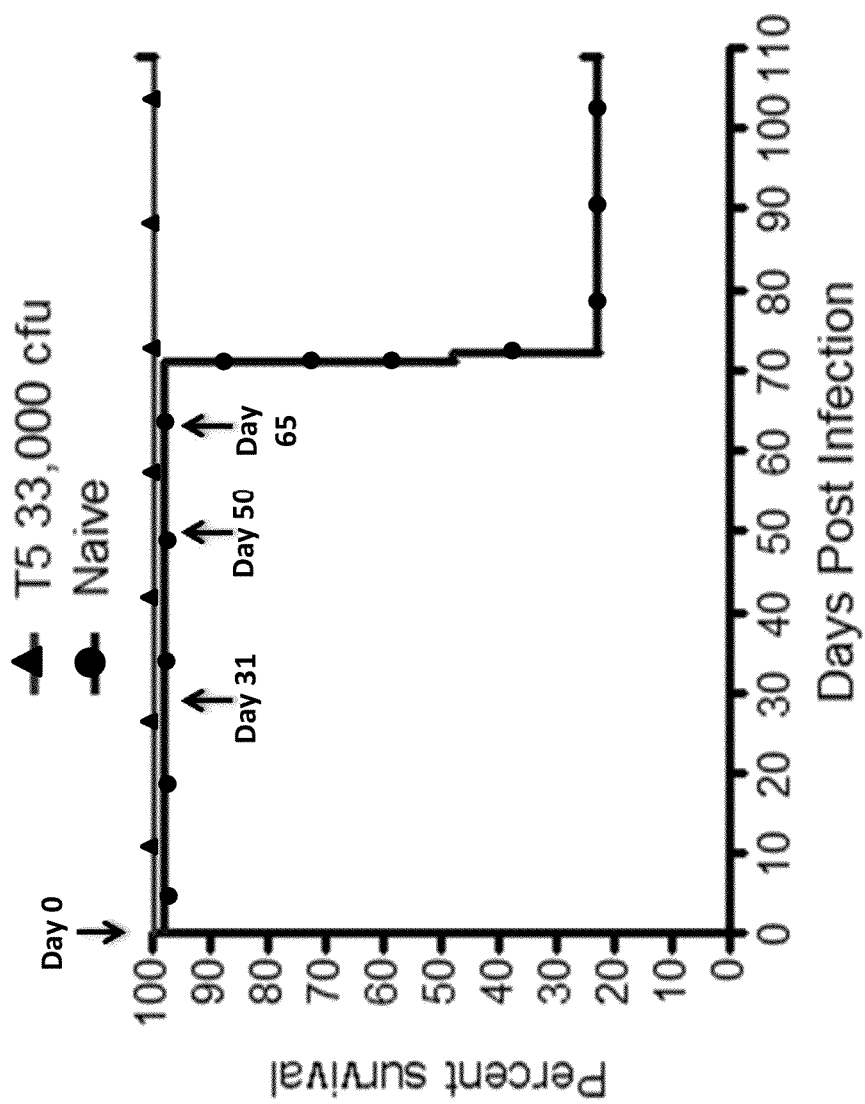
FIG. 6 is a Kaplan-Meier plot of C57BL6 mice immunized with T5 (SEQ ID NO. 1) *F. tularensis* LVS prior to challenge with wild type *F. tularensis* Schu4.

In one experiment, four each of C57BL6 mice were either primed by exposure to 33,000 cfu *F. tularensis* LVS T5 mutant on day 0 via an intratracheal inhalation gasp reflex administration or remained naïve. No illness was observed. The four LVS T5 immunized mice were boosted with 300,000 cfu T5 mutant at day 31 and day 50. As shown in FIG. 6, despite challenge with a dose 60-fold greater than a normal lethal dose, all animals were completely healthy. All four primed and dually-boosted mice together with the naïve mice were challenged with 50 cfu wild type *F. tularensis* Schu4 at day 65. As seen in FIG. 6, all immunized mice survived the Schu4 challenge to at least day 110 when the study was terminated. Three of four naïve mice died within seven days of the *F. tularensis* Schu4 challenge; it is assumed that the one surviving mouse did not receive proper infection.

Figure 7:
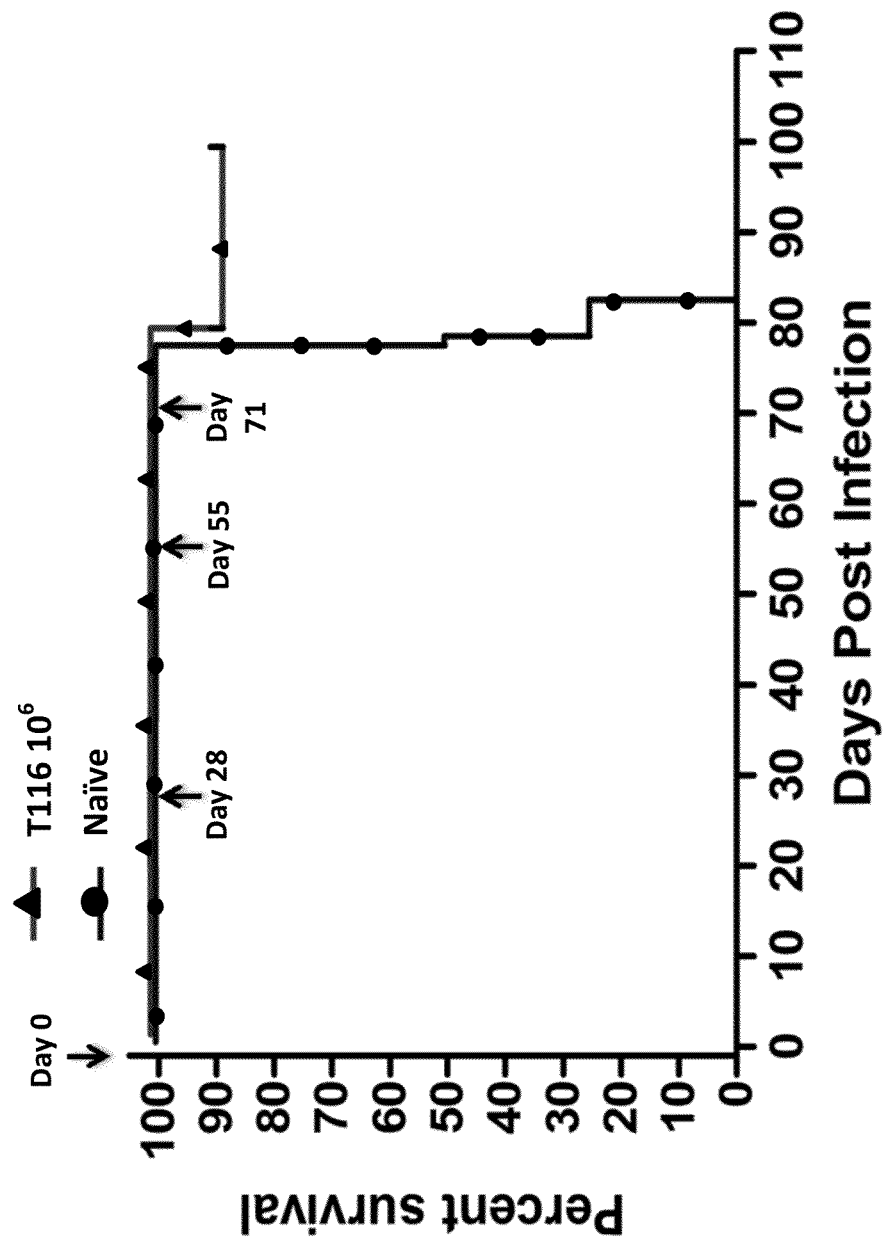
FIG. 7 is a Kaplan-Meier Plot of C57BL6 mice immunized with T116 *F. tularensis* (SEQ ID NO. 2) Schu4 prior to challenge with wild type *F. tularensis* Schu4.

In an analogous experiment shown in FIG. 7, 12 C57BL6 mice were primed with a dose of $10^6$ cfu *F. tularensis* Schu4 mutant T116 (SEQ ID NO. 2) via intratracheal inhalation gasp reflex administration on day 0. 12 animals were left naïve. The challenged animals showed modest symptoms (lethargy, withdrawal), but despite challenge with a dose $10^5$-fold greater than a normal lethal dose, all animals were completely healthy post-challenge. On day 28 in a dose escalation, the primed animals were boosted with $10^7$ cfu mutant T116 (SEQ ID NO. 2). After eleven days, four animals succumbed to infection. The eight surviving animals were re-challenged with $10^6$ cfu of mutant T116 (SEQ ID NO. 2) on day 55, from which all animals subsequently survived. On day 71, the immunized animals together with the naïve controls were challenged with 10 cfu wild type *F. tularensis* Schu4. As seen in FIG. 7, all naïve animals succumbed to the challenge by day 11, while only one of eight immunized animals succumbed to the challenge. The remaining seven mice survived up to 28 days post-wild type *F. tularensis* Schu4 challenge when the experiment was terminated.

In a separate experiment (not shown) animals primed with $10^6$ cfu *F. tularensis* Schu4 mutant T116 (SEQ ID NO. 2) on day 0 and boosted on day 21 were challenged with 50 cfu of *F. tularensis* Schu4 on day 36. All immunized animals survived this challenge with wild type for 50 days when the study was terminated. Thus, the impaired mutants appear to identify rationally attenuated targets that are capable of inducing immune protection against pulmonary challenge of wild type Schu4.

Although specific exemplary embodiments have been described in detail in the foregoing description and illustrated in the drawings, various other embodiments, changes, and modifications to the disclosed embodiment(s) will become apparent to those skilled in the art. All such other embodiments, changes, and modifications are intended to come within the spirit and scope of the appended claims.

What is claimed is:

1. A live strain of *Francisella tularensis* Schu4, wherein a gene selected from the group consisting of priA and purA is inactivated.

2. The live strain of claim 1, wherein the gene is inactivated by an insertional mutation.

3. The live strain of claim 1, wherein the gene is inactivated by deletion of at least a portion of the gene.

4. A pharmaceutical composition comprising:
   the live strain of claim 1; and
   a pharmaceutically acceptable carrier.

5. A method of conferring immunity against a virulent strain of *Francisella tularensis* Schu4, the method comprising:
   administering a first amount of the live strain of *Francisella tularensis* Schu4 of claim 1 to an animal such that an immune response against said virulent strain of *Francisella tularensis* Schu4 is produced in the animal.

6. The method of claim 5, further comprising:
   administering a second amount of the live strain of *Francisella tularensis* Schu4 to an animal, wherein the second amount is administered at a predetermined amount of time following administration of the first amount.

7. A method of conferring immunity against a virulent strain of *Francisella tularensis* Schu4, the method comprising:
   administering an effective amount of the pharmaceutical composition of claim 4 to an animal such that an immune response against said virulent strain of *Francisella tularensis* Schu4 is produced in the animal.

8. A live strain of *Francisella tularensis* LVS, wherein a gene selected from the group consisting of priA and purA is inactivated.

9. The live strain of claim 8, wherein the gene is inactivated by an insertional mutation.

10. The live strain of claim 8, wherein the gene is inactivated by deletion of at least a portion of the gene.

11. A pharmaceutical composition comprising:
   the live strain of claim 8; and
   a pharmaceutically acceptable carrier.

12. A method of conferring immunity against a virulent strain of *Francisella tularensis* LVS, the method comprising:
   administering a first amount of the live strain of *Francisella tularensis* LVS of claim 8 to an animal such that an immune response against said virulent strain of *Francisella tularensis* LVS is produced in the animal.

13. The method of claim 12, further comprising:
   administering a second amount of the live strain of *Francisella tularensis* LVS to an animal, wherein the second amount is administered at a predetermined amount of time following administration of the first amount.

14. A method of conferring immunity against a virulent strain of *Francisella tularensis* LVS, the method comprising:
   administering an effective amount of the pharmaceutical composition of claim 11 to an animal such that an immune response against said virulent strain of *Francisella tularensis* LVS is produced in the animal.

\* \* \* \* \*